Figure 1:
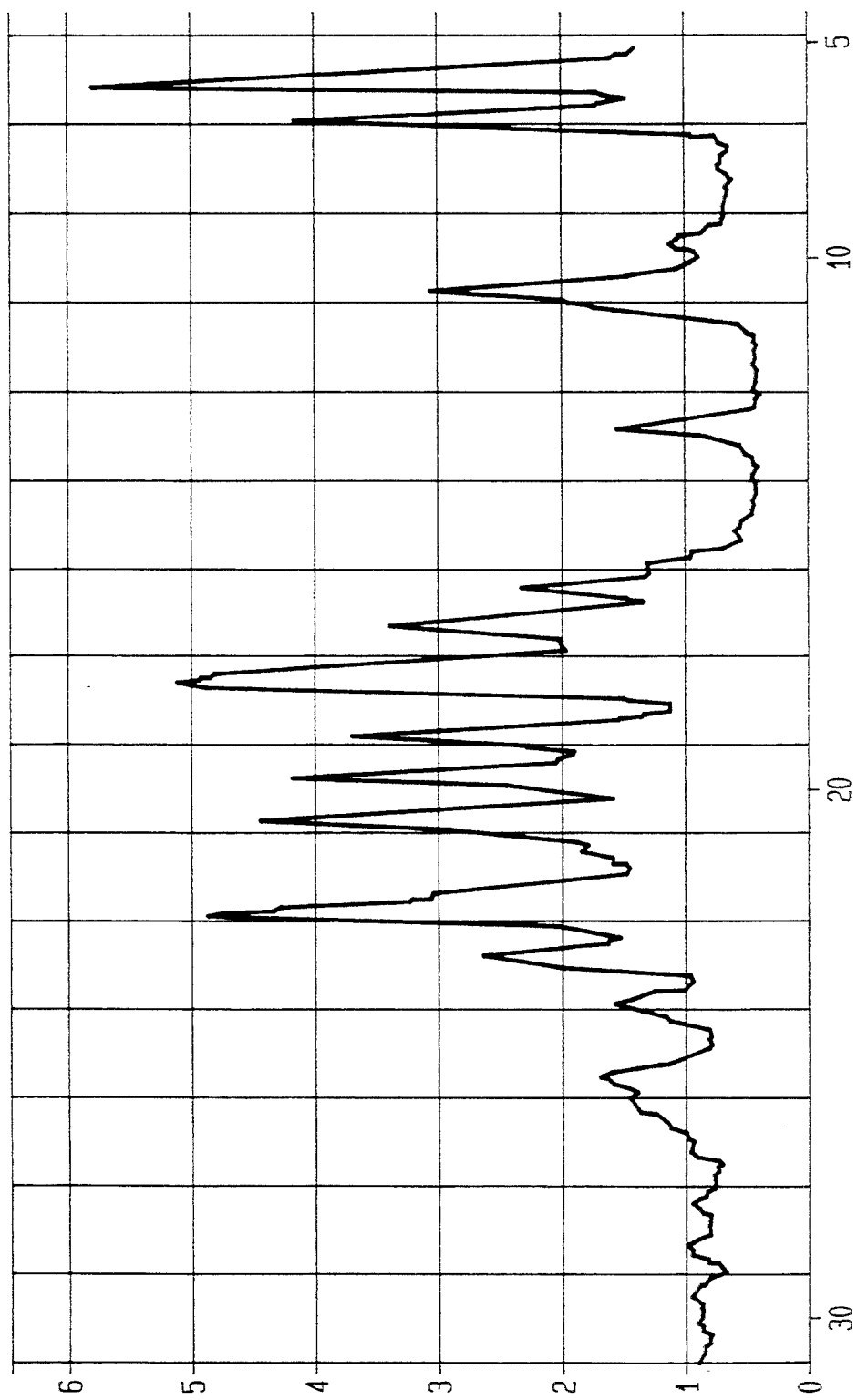

United States Patent [19]

Baker et al.

[11] Patent Number: 5,436,266
[45] Date of Patent: * Jul. 25, 1995

[54] COMPOUNDS

[75] Inventors: Geoffrey H. Baker, Banstead; Merle Beal, Horley, both of England

[73] Assignee: Beecham Group p.l.c., Brentford, England

[*] Notice: The portion of the term of this patent subsequent to Apr. 10, 2007 has been disclaimed.

[21] Appl. No.: 203,681

[22] Filed: Feb. 28, 1994

Related U.S. Application Data

[60] Continuation of Ser. No. 920,120, Jul. 24, 1992, abandoned, which is a division of Ser. No. 468,584, Mar. 12, 1990, Pat. No. 5,191,093, which is a division of Ser. No. 338,446, Apr. 13, 1989, Pat. No. 4,916,155, which is a continuation of Ser. No. 72,683, Jul. 13, 1987, abandoned, which is a continuation of Ser. No. 745,213, Jun. 17, 1985, abandoned.

[30] Foreign Application Priority Data

Jun. 19, 1984 [GB] United Kingdom ................ 8415579

[51] Int. Cl.⁶ ..................... A61K 31/35; C07D 309/10
[52] U.S. Cl. ..................... 514/460; 549/414
[58] Field of Search .................. 549/414; 514/460

[56] References Cited

U.S. PATENT DOCUMENTS 4,289,703 9/1981 Barrow et al. ................ 549/414

FOREIGN PATENT DOCUMENTS 5614 11/1979 European Pat. Off. ............ 549/414
2097670 11/1982 United Kingdom ................ 549/414

OTHER PUBLICATIONS

Isagi et al., C.A. 87:182,603a (1977).

*Primary Examiner*—Nicky Chan
*Attorney, Agent, or Firm*—Hopgood, Calimafde, Kalil & Judlowe

[57] ABSTRACT

Crystalline calcium pseudomonate or a hydrate thereof, in particular the dihydrate. Processes for the preparation of these salts and their use in human and veterinary medicine and as a growth promoter in animals are described.

9 Claims, 4 Drawing Sheets

COMPOUNDS

This application is a continuation of application Ser. No. 920,120, filed Jul. 24, 1992, abandoned, which is a divisional of Ser. No. 468,584, filed Mar. 12, 1990, now U.S. Pat. No. 5,191,093, which is a division of Ser. No. 338,446, filed Aug. 13, 1989, now U.S. Pat. No. 4,916,155, which is a continuation of Ser. No. 72,683, filed Jul. 13, 1987, abandoned, which is a continuation of Ser. No. 745,213, filed Jun. 17, 1985, abandoned.

The present invention relates to crystalline calcium pseudomonate, a process for its production, and its use in human and veterinary medicine and as a growth promoting agent in animals.

Pseudomonic acid is an antibiotic produced by aerobically culturing *Pseudomonas fluorescens*. The compound, of formula (I) below, and its salts and esters are disclosed and claimed in U.K. Patent No. 1 395 907.

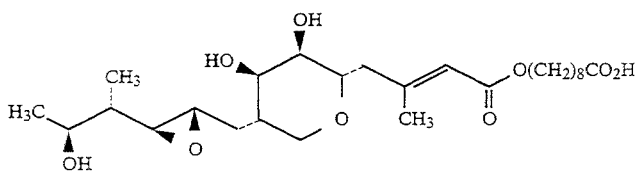

(I)

The calcium salt of pseudomonic acid is disclosed in UK Patent Nos. 1,577,545 and 1,577,730.

The readily isolable amorphous form of this salt has been found to be a sparingly water soluble material having a low melting point and poor thermal stability.

It has now been found that calcium pseudomonate, when isolated in a crystalline form, has a high melting point and shows outstandingly good thermal stability relative both to the amorphous calcium pseudomonate and to pseudomonic acid itself.

Crystalline calcium pseudomonate has not been specifically disclosed in the above patents or any other publications and is, therefore, novel.

Accordingly the present invention provides crystalline calcium pseudomonate or a hydrate thereof.

In a further aspect the invention provides crystalline calcium pseudomonate or a hydrate thereof, substantially free of amorphous calcium pseudomonate.

A preferred crystalline calcium pseudomonate hydrate is the dihydrate.

Suitably calcium pseudomonate dihydrate in crystalline form, substantially free of amorphous calcium pseudomonate provides a powder X-ray diffractogram (using copper Kα radiation) substantially as shown in FIG. 1.

Figure 2:
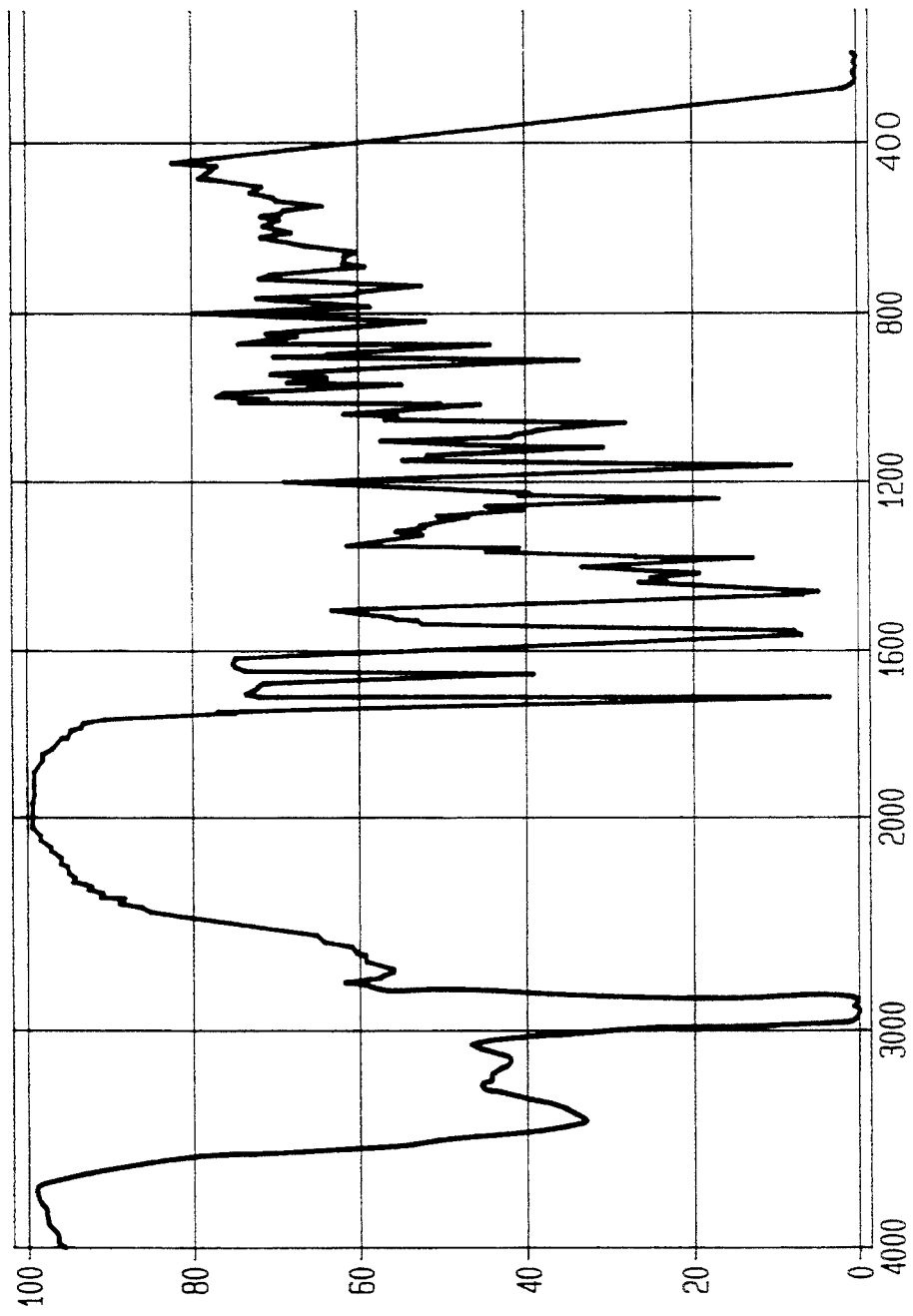

Suitably the calcium pseudomonate dihydrate in crystalline form and substantially free of amorphous calcium pseudomonate provides an infra red spectrum (in nujol) substantially as shown in FIG. 2.

Figure 3:
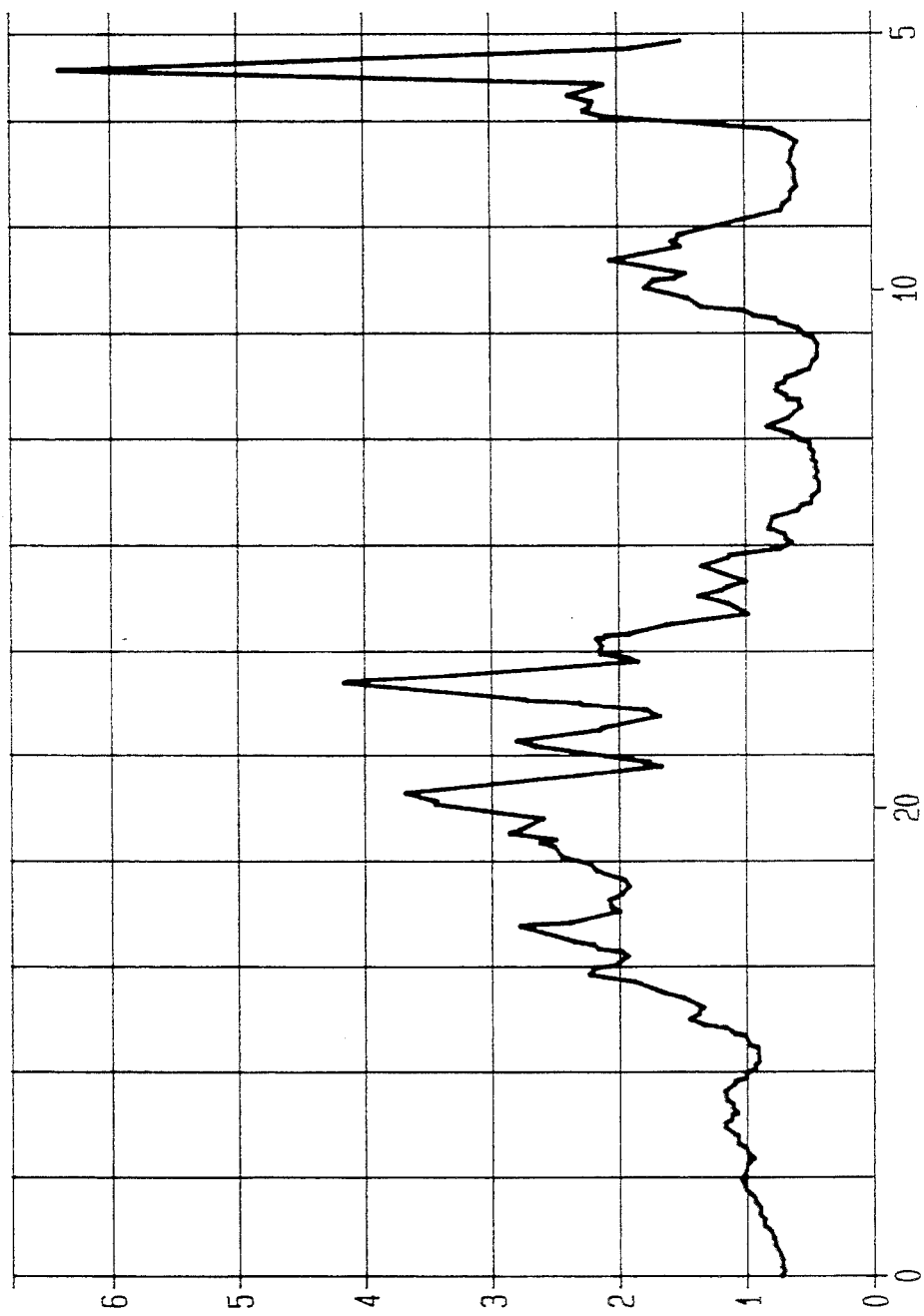
Figure 4:
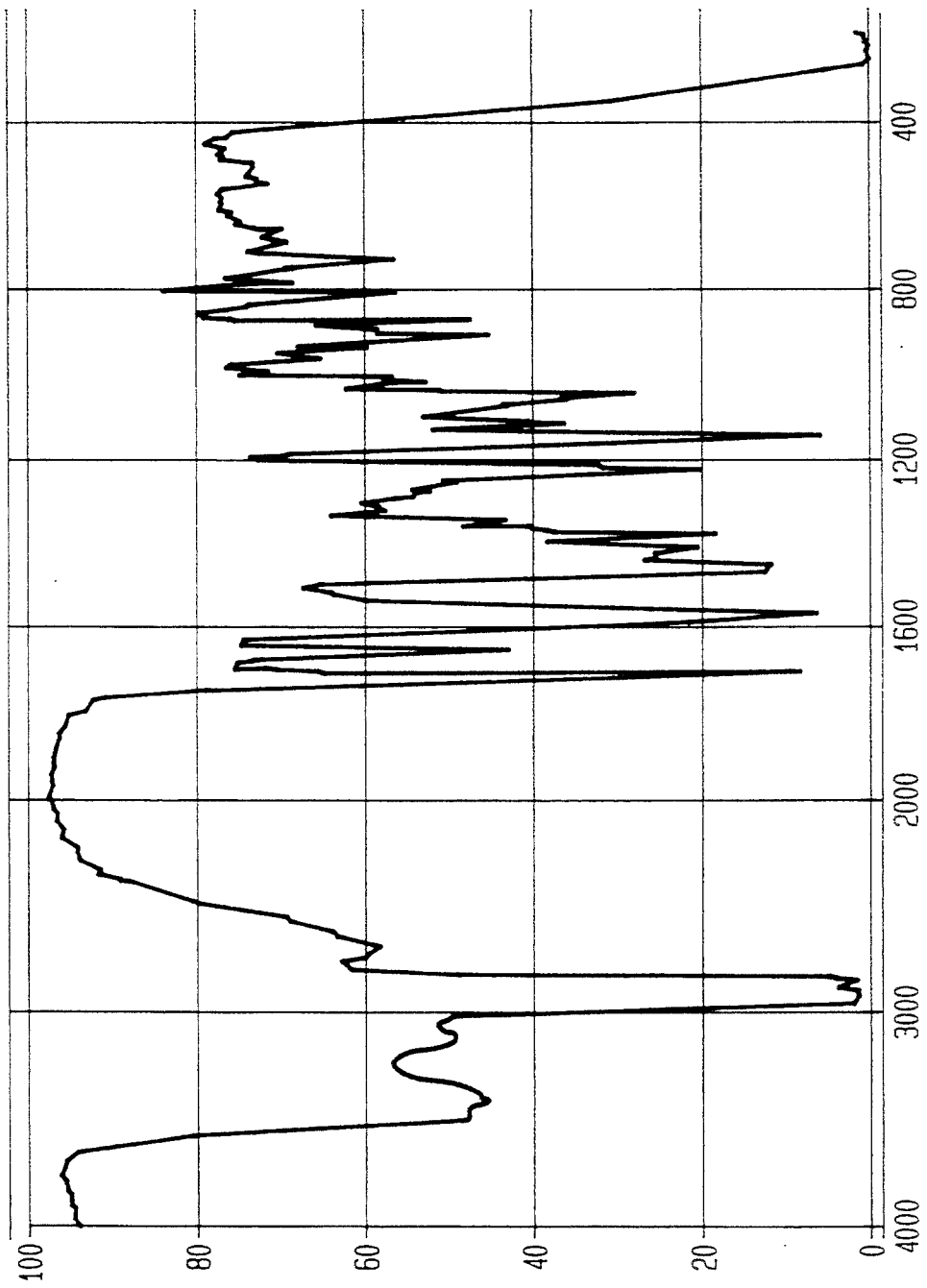

Anhydrous crystalline calcium pseudomonate, when substantially free of amorphous calcium pseudomonate provides a powder X-ray diffractogram (using copper Kα radiation) substantially as shown in FIG. 3 and an infra red spectrum (in nujol) substantially as shown in FIG. 4.

As used herein, the expression "anhydrous crystalline calcium pseudomonate" refers to crystalline calcium pseudomonate substantially free of water of crystallisation, for example containing less than 0.5% by weight of water.

Suitably the anhydrous crystalline calcium pseudomonate, substantially free of amorphous calcium pseudomonate has a melting point within the range of 105° to 1370° C., preferably within the range of 125° to 137° C., more preferably within the range of 130° to 135° C.

The invention also provides crystalline calcium pseudomonate or a hydrate thereof for use in the treatment of the human or animal body.

The invention further provides a process for preparing crystalline calcium pseudomonate or a hydrate thereof which process comprises reacting pseudomonate ions with calcium ions in solution in an aqueous solvent, recovering a crystalline calcium pseudomonate hydrate from the solution, and thereafter if desired removing water of crystallisation.

Suitably the process is effected by adding a source of calcium ions to an aqueous solution of pseudomonic acid or a pseudomonate salt.

Suitably the solution of pseudomonic acid or pseudomonate ions is the product of aerobically culturing Pseudomonas fluroescens (NCIB 10586). Such a solution may be the culture medium in which the organisms have been grown or it may have been produced by purifying such a medium for instance by extracting pseudomonic acid from such a culture medium using a polar, organic, water-immiscible solvent as described in EP 0 005 614 and subsequently re-extracting the pseudomonic acid into aqueous solution, preferably into mild alkaline aqueous solution. Alternatively the solution of pseudomonic acid or pseudomonate ions may be produced by dissolving pseudomonic acid or a salt thereof, in an aqueous solvent.

The aqueous solvent for the process may be water or a mixture of water and an organic cosolvent.

The organic cosolvent may be water miscible or water immiscible. Preferably the organic cosolvent is water miscible.

Suitable organic cosolvents are methanol, propanol and acetone.

Preferred organic cosolvents are methanol and acetone.

The crystalline calcium pseudomonate hydrate is suitably recovered in the form of the dihydrate.

Recovery of the calcium pseudomonate dihydrate is suitably achieved by crystallization or precipitation from the aqueous solvent, preferably from water.

When the aqueous solvent is a mixture of water and an organic cosolvent, recovery may be facilitated by dilution of the aqueous solution with water or by selective removal of the organic cosolvent. A preferred form of selective removal is evaporation.

In a preferred form of the process a solution of pseudomonic acid in aqueous solvent is reacted with a source of calcium ions. A preferred source of calcium ions is calcium oxide.

Suitably the aqueous solvent is a mixture of water and methanol, the methanol being selectively removed prior to recovery, preferably by evaporation.

Preferably the calcium pseudomonate dihydrate is recovered via precipitation or crystallization, preferably from water.

In an alternative preferred form of the process a solution of a salt of pseudomonic acid in aqueous solvent is reacted with a source of calcium ions, preferably a soluble calcium salt. Preferred salts of pseudomonic acid are the lithium, sodium and potassium salts. A particularly preferred salt is the sodium salt.

Suitably the soluble calcium salt is calcium chloride, or calcium acetate, preferably calcium chloride.

Preferably calcium pseudomonate dihydrate is recovered by precipitation or crystallization, preferably from water.

Calcium pseudomonate dihydrate may also be prepared by dissolving calcium pseudomonate in an aqueous solvent and thereafter recovering the dihydrate by crystallization or precipitation, preferably from water.

The water of crystallisation can be removed from the crystalline hydrate so produced to give crystalline anhydrous calcin pseudomonate.

Suitably the water of crystallisation is removed by heating the crystalline calcium pseudomonate hydrate, preferably the dihydrate, to a temperature sufficient to remove the water from the hydrate, preferably above 70° C.

Alternatively the crystalline calcium pseudomonate hydrate can be dried in vacuo in the presence of a drying agent such as phosphorous pentoxide. Temperatures of from 18°–80° C. are suitably employed preferably for a period of about 21 hours.

Conversely the crystalline calcium pseudomonate can be left to equilibrate to form the dihydrate by exposure to the atmosphere.

When used herein the term 'calcium pseudomonate' refers to that form of the calcium salt which is amorphous and not hydrated.

Published UK Patent Application No.2097670 discloses the use of pseudomonic acid and its salts and esters as a growth promoter for livestock. The surprising thermal stability of crystalline calcium pseudomonate is considered to provide a more stable form of pseudomonic acid for use as a growth promoter, particularly in the formulations of the drug which involve elevated temperatures. Accordingly, the present invention provides a method for improving the weight gain and feed utilisation efficiency of livestock, which method comprises administering to livestock a growth promoting, non-toxic amount of crystalline calcium pseudomonate or a hydrate thereof.

Preferably crystalline calcium pseudomonate dihydrate is employed in the method. Crystalline calcium pseudomonate or a hydrate thereof may be administered to any livestock for example pigs, poultry and ruminants such as cattle and sheep. It is particularly suitable for improving the weight gain and feed utilisation efficiency of pigs.

Crystalline calcium pseudomonate or a hydrate thereof, preferably the dihydrate, may be administered orally, preferably in the feedstuff or drinking water provided for the livestock. Conveniently it is administered in the feedstuff at from 2 to 300 ppm suitably less than 100 ppm, for example from 10 to 40 ppm.

For administration in feedstuff crystalline calcium pseudomonate or a hydrate thereof, preferably the dihydrate, is conveniently formulated as a premix in association with a suitable carrier.

Accordingly in a further aspect, the present invention provides a veterinarily acceptable premix formulation comprising crystalline calcium pseudomonate or a hydrate thereof, preferably the dihydrate, in association with a veterinarily acceptable carrier.

Suitable carriers are inert conventional agents such as powdered starch. Other conventional premix carriers may also be employed.

The infections in humans against which the compounds of this invention are particularly useful include sexually transmitted disease; infections of the respiratory tract; bacterial meningitis; and skin and soft tissue infections.

In animals they may be employed for the treatment of mastitis in cattle, for swine dysentery, and for mycoplasma infections and eye infections in animals such as turkeys, chickens, pigs and cattle.

Some of the human and veterinary diseases either caused by mycoplasma species or in which they play a prominent role, and against which the compounds of this invention are effective, are as follows:

Avian
*M. gallisepticum*—chronic respiratory diseases (air-sacculitis) of chickens and turkeys Bovine
*M. bovis*—mastitis, respiratory disease and arthritis of cattle
*M. dispar*—calf pneumonia Porcine
*M. hyopneumoniae*—enzootic pneumonia of pigs
*M. hyorhinis*—arthritis in pigs
*M. hyosynoviae*

Human
*M. pneumoniae*—primary atypical pneumonia

The compounds of the present invention are particularly useful in the treatment of mycoplasmal and/or bacterial pneumonia in animals such as pigs, cattle and sheep, because they also have activity against the bacteria *Bordetella bronchiseptica, Pasteurella multocida* and *Haemophilus spp,* which are often involved in the disease.

This invention also provides a pharmaceutical or veterinary composition which comprises crystalline calcium pseudomonate or a hydrate thereof (hereinafter referred to as the 'drug') together with a pharmaceutically or veterinarily acceptable carrier or excipient.

The compositions may be formulated for administration by any route, and would depend on the disease being treated. The compositions may be in the form of tablets, capsules, powders, granules, lozenges, liquid or gel preparations, such as oral, topical or sterile parenteral suspensions.

Tablets and capsules for oral administration may be in unit dose presentation form, and may contain conventional excipients such as binding agents, for example syrup, acacia, gelatin, sorbitol, tragacanth, or polyvinyl-pyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin, hydrogenated edible fats; emulsifying agents, for example lecithin, sorbitan monooleate, or acacia: non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin the drug may be made up into a cream, lotion or ointment. Cream or ointment formulations that may be used for the drug are conventional formulations well known in the art, for example, as described in standard text books of pharmaceutics and cosmetics, such as Harry's Cosmeticology published by Leonard Hill Books, and the British Pharmacopoeia. These-formulations may, if desired, be incorporated into a tulle.

These formulations may comprise additional therapeutic agents such as antibacterial, antifungal, antiviral and antiinflammatory agents, for instance chlortetracycline, miconazole, idoxuridine and phenazone.

Suppositories will contain conventional suppository bases, e.g. cocoa-butters or other glyceride. For parenteral administration, fluid unit dosage focas are prepared utilizing the drug and a sterile vehicle, The drug, depending on the vehicle and concentration used, can be suspended in the vehicle. Advantageously, adjuvants such as a local anaesthetic, preservative and buffering agents can be dissolved in the vehicle. To enhance the stability the composition can be frozen after filling into the vial and water removed under vacuum. The dry lypophilized powder is then sealed in the vial. The drug can be sterilised by exposure to ethylene oxide before suspending in the sterile vehicle. Advantageously, a surfactant or wetting agent is included in the composition to facilitate uniform distribution of the drug.

For topical application to the ear, the drug may be made up into a suspension in a suitable liquid carrier, such as water, glycerol, diluted ethanol, propylene glycol, polyethylene glycol or fixed oils.

For topical application to the eye, the drug is formulated as a suspension in a suitable, sterile aqueous or non-aqueous vehicle. Additives, for instance buffers such as sodium metabisulphite or disodium edetate; preservative's including bactericidal and fungicidal agents, such as phenylmercuric acetate or nitrate, benzalkonium chloride or chlorhexidine, and thickening agents such as hypromellose may also be included.

The drug may also be applied to the skin by aerosol.

The dosage employed for compositions administered topically will, of course, depend on the size of the area being treated. For the ears and eyes each dose will typically be in the range from 10 to 100 mg of the drug.

Veterinary compositions for intramammary treatment of mammary disorders in animals, especially bovine mastitis, will generally contain a suspension of the drug in an oily vehicle.

The compositions may contain from 0.1% to 99% by weight, preferably from 10–60% by weight, of the drug, depending on the method of administration. Where the compositions are in unit dose form, each dosage unit will preferably contain from 50–500 mg, of the drug. The dosage as employed for adult human treatment will preferably range from 100 mg to 3 g, per day, for instance 250 mg to 2 g of the drug per day, depending on the route and frequency of administration.

Alternatively, the drug may be administered as part of the total dietary intake. In this case the amount of drug employed may be less than 1% by weight of the diet and is preferably no more than 0.5% by weight. The diet for animals may consist of normal foodstuffs to which the drug may be added or the drug may be included in a premix for admixture with the foodstuff.

A suitable method of administration of the drug to animals is to add it to the animals' drinking water. In this case a concentration of the drug in the drinking water of about 5–500 mg/ml, for example 5–200 µg/ml, is suitable.

The present invention further provides a method of treating bacterial or mycoplasmal infections in humans or non-human animals which method comprises administering to a human or non-human animal in need thereof an effective non-toxic amount of crystalline calcium pseudomonate or a hydrate thereof.

Particular bacterial and/or mycoplasmal infections of human or non-human animals which can be treated in this way, include venereal disease, respiratory infections such as bacterial bronchitis, bacterial meningitis, non-specific urethoitis and pneumonia in humans, respiratory infections, mastitis, swine dysentery and pneumonia in animals.

The following Examples illustrate the invention.

Example 1

Calcium pseudomonate dihydrate

To a solution of pseudomonic acid (100 g, 0.2 mole) in 50% aqueous methanol (1.5 l) was added portion-wise calcium oxide (7.1 g, 0.127 mole) to give a neutral solution (pH 7.0). The solution was stirred at room temperature for 1 h before evaporation of the solvent at reduced pressure to give a foam. The foam was added portion-wise with stirring to water (2 l) at room temperature. After stirring for 1 h the solution was filtered and the filtrate allowed to stand for 48 h at room temperature. The crystalline product was filtered off to give the title compound (31.0 g, 29%), m.p. 135°–137° C.; $\gamma_{max}$(KBr) 3600–3100, 1710, 1650 and 1600–1530 cm$^{-1}$; $\lambda_{max}$ (EtOH) 220 nm ($\epsilon_{max}$ 30840); $\delta_H$ (CD$_3$OD) 5.75 (1H, s, 2-H), 4.08 (2H, t, 9'-H$_2$), 3.9–3.7 (4H, m, 5-H, 7-H, 13-H, 16$_a$-H), 3.58 (1H, m, 16$_b$-H), 3.37 (1H, dd, 6-H), 2.8 (1H, m, 10-H), 2.7 (1H, dd, 11-H), 2.6 (1H, m, 4$_a$-H), 2.22 (3H, m, 4-H, 2'-H$_2$), 2.2 (3H, s, 15-H$_3$), 1.95 (1H, m, 8-H), 1.75–1.5 (6H, m, 9- 2, 3'-H$_2$, 8'H$_2$), 1.4–1.3 (9H, m, 12-H, 4' -H$_2$, 5'-H$_2$, 6'-H$_2$, 7'-H$_2$), 1.22 (3H, d, 14-H$_3$) and 0.95 (3H, d, 17-H$_3$); $\delta_C$(CD$_3$OD) 184.5 (C-1'), 168.1 (C-1), 159 (C-3), 118.2 (C-2), 76 (C-5), 71.6 (C-13), 70.6 (C-7), 69.9 (C-6), 66.2 (C-16'), 64.7 (C-9'), 61.2 (C-11), 56.8 (C-10), 43.8 (C-4), 43.6 (C-12), 41.4 (C-8), 38.5 (C-2°), 32.9 (C-9), 30.7, 30.5, 30.3, (C-4', 5' and 6'), 29.8 (C-8'), 27.2, 27.1 (C-3' and 7'), 20.4 (C-14), 19.4 (C-15) and 12.3 ppm (C-17) (Found: C, 57.97; H, 8.35; Ca, 3.68. C$_{52}$H$_{86}$O$_{18}$Ca.2H$_2$O requires C, 58.08; H, 8.44; Ca, 3.73%. Water content, found: 3.70. 2H$_2$O requires 3.35%). The mother liquors from the crystallization were evaporated at reduced pressure to half volume to give on standing for 24 h a second yield of calcium pseudomonate dihydrate (39 g, 36%) m.p. 132°–134° C. (water content 3.44%).

Example 2

Calcium pseudomonate dihydrate

Pseudomonic acid (93%) (1400 g, 2.6 mole) was dissolved in methanol (7 1) and filtered before careful dilution with water (5 1). To the stirred solution of pseudomonic acid was added portionwise calcium oxide (92 g, 1.64 mole). When the pH of the solution reached 7, the mixture was filtered to give a clear yellow solution which had risen to pH 7.9. After evaporation of the methanol under reduced pressure to give a final volume of 5.6 1 the solution was diluted with water (400 ml) and allowed to crystallise. After standing for 24 h the mixture was again diluted with water 2.5 1) and crystallisation continued for 18 h. The crystalline product was stirred to give a slurry which was filtered and the collected product was washed by slurrying with water (2.5 1). The white granular product was filtered off and dried overnight in a fan-assisted oven at room temperature. The product was lightly ground before drying in a fluidised bed air dryer for 2 h at room temperature to yield calcium pseudomonate dihydrate (1125 g, 80%) m.p. 135° C.; Found: water, by Karl Fischer, 3.6%; $2H_2O$ requires 3.35%.

The preparation was repeated and yields of (1300 g, 93%) and 1275 g, 91%) were obtained.

Example 3

Calcium pseudomonate dihydrate

To a filtered solution of pseudomonic acid (200 g, 0.4 mole) in methanol (1 1) and water (750 ml) was added portionwise calcium oxide (13.5 g, 0.24 mole) to give a neutral solution (pH 7.2). The solution was filtered and the methanol evaporated from the filtrate under reduced pressure. The aqueous concentrate was diluted to a volume of approximately 1 liter and left to crystallise for 24 h at room temperature. The white crystalline product was filtered off and washed with water (500 ml) and dried at 55° C. under reduced pressure. The product was then allowed to equilibrate under atmospheric conditions for 12 h to give crystalline calcium pseudomonate dihydrate (165 g, 77%) m.p. 125°–132° C. (water content (Karl Fischer) 3.4%).

Example 4

Calcium pseudomonate dihydrate

Pseudomonic acid (1.0 g, 2.0 mmole) was stirred in water (20 ml) and neutralised slowly with sodium hydroxide solution (1.8 ml, 1M) (pH 7.1). Calcium chloride (0.25 g, 2.25 mmole) was added to the mixture and stirring maintained to give a clear solution. After standing for 18 h the crystalline product was filtered off, washed with water (5 ml) and dried to give calcium pseudomonate dihydrate (0.5 g, 48%), m.p. 133°–136° C.

Example 5

Calcium Pseudomonate Dihydrate

Pseudomonic acid (100 gms) was dissolved in a mixture of acetone/water (100 ml and 50 ml respectively). Sodium hydroxide solution (10% w/v) and further water were added to give an approximate 10–12% w/v solution of the sodium salt at pH 8. Calcium chloride (23 gms) in aqueous solution is added, seeding as necessary and the calcium pseudomonate was allowed to crystallise at 20°–30° C. The product was then isolated, washed and dried to yield 100 gms of the crystalline dihydrate.

Example 6

Calcium Pseudomonate Dihydrate

Pseudomonic Acid whole broth was extracted with methyl isobutylketone. The organic extract was then concentrated and back-extracted into aqueous sodium hydroxide to pH 8.

The resultant back-extract was concentrated if necessary to give an ca 10% w/v solution of sodium pseudomonate. Calcium pseudomonate dihydrate was then produced by the addition of a suitable precipitant as per Example 5.

Example 7

Crystalline Anhydrous Calcium Pseudomonate

Crystalline calcium pseudomonate dihydrate (15g) was dried in vacuo over phosphorus pentoxide at a temperature of 80° C. for a period of 21 hours to give crystalline calcium pseudomonate substantially free of water of crystallisation m.p. 131°–133° C. (water content (Karl Fischer) 0.3%).

Description 1

Amorphous anhydrous

Calcium pseudomonate A

To a solution of pseudomonic acid A (35 g, 0.07 mole) in 50% aqueous methanol (0.51) was added portionwise calcium oxide (2.75 g, 0.049 mole) to give a neutral solution (pH.7.1). The solution was stirred at room temperature for 1 h, filtered and filtrate evaporated under reduced pressure to give a solid foam. The foam was triturated with dry ether (0.51) for 1 h before filtering to give the title compound as a white powder (33g, 90%) m.p. 70°–76° C.; $\gamma_{max}$ (KBr) 3600–3100, 2915, 1710, 1650 and 1600–1530 cm $^{-1}$; $<_{max}$ (EtOH) 220 nm ($\epsilon_m$ 29840); $\delta_H$(CD$_3$OD) 5.75 (1H, s, 2-H), 4.08 (2H, t, 9'-H$_2$), 3.9–3.7 (4H, m, 5-H, 7-H, 13-H, 16a-H), 3.58 (1H, m, 16b-H), 3.37 (1H, dd, 6-H), 2.8 (1H, m, 10-H), 2.7 (1H, dd, 11-H), 2.6 (1H, m, 4$_a$-H), 2.22 (3H, m, 4$_b$-H, 2'-H$_2$), 2.2 (3H, s, 15-H$_3$), 1.95 (1H, m, 8-H), 1.75–1.5 (6H, m, 9-H$_2$, 3'-H$_2$, 8'-H$_2$), 1.4–3 (9H, m, 12-H, 4'-H$_2$, 5'-H$_2$, 6'-H$_2$, 7'-H$_2$), 1.22 (3H, d, 14-H$_3$) and 0.95 (3H, d, 17-H$_3$); $\delta_C$(CD$_3$OD) 168.1 (C-1), 158.9(C-3), 118.2 (C-2), 76.1 (C-13), 70.7 (C-7), 69.9 (C-6), 66.3 (C-! 6), 64.7 (C-9), 61.3 (C-11), 56.8 (C-10), 43.8 (C-4), 43.6 (C-12), 41.4 (C-8), 38.1 (C-2'), 32.9(C-9), 30.6, 30.5, 30.3 (C-4', 5', and 6'), 29.8 (C-8'), 27.0 (C-3' and 7'), 20.4 (C-14), 19.4 (C-15) and 12.3ppm (C-17); m/e (rel.int.) (+ve ion FAB) 539 ](pseudomonate ) Ca]+, 78%](Found: C, 60.16; H, 8.77; Ca, 3.86. $C_{52}H_{86}O_{18}Ca$ requires C, 60.09; H, 8.34; Ca, 3.86%).

Thermal stability data: for crystalline calcium pseudomate dihydrate, amorphous calcium pseudomonate and pseudomonic acid.

| Sample | Crystalline Calcium Dehydrate Salt | Anhydrous Amorphous Calcium Salt | Pseudomonic Acid |
|---|---|---|---|
| Melting Point | 125–137° C. (as anhydrous) | 70–76° C. | 73–75° |
| Percentage Purity of batch* | 92.1 | 89.9 | 91.9 |

| Sample | Crystalline Calcium Dehydrate Salt | Anhydrous Amorphous Calcium Salt | Pseudomonic Acid |
|---|---|---|---|
| Percentage Initial Potency after Storage** | | | |
| 10 days 50° C. | 98.9 | 83.3 | 77.9 |
| 8 days 80° C. | 97 | 29 | 0 |
| 2 weeks | | | |
| 37° C. | 100.2 | 97.7 | 98.6 |
| 50° C. | 98.7 | 80.1 | 55.7 |
| 80° C. | 94 | 14 | 0 |

*Expressed as percentage of pure free pseudomonic acid.
**Expressed as percentage of initial purity.

Biological Data a) Mycoplasma

The activity of the compounds of the Examples against various mycoplasmal organisms was assayed in vitro in Friis broth solidified with 0.9% agarose and inoculated with $10^3$ to $10^5$ C.F.U. The minimum inhibitory concentrations (MIC's) were determined after incubation for 6 days at 37° C. and are shown in Table 1.

b) Veterinary Bacteria

The activity of the compounds of the Examples against various veterinarily important bacteria, was assayed vitro using two-fold serial dilutions in Diagnostic Sensitivity Test Agar inoculated with $10^4$ organisms. The MIC's were determined after incubaltion for 18 hours at 37° C. and are shown in Table 2.

c) Human Bacteria

The activity of the compounds of the Examples against various bacteria which are important in diseases of humans, was assayed in vitro using serial dilutions in nutrient agar with 5% chocolated horse blood. The MIC's were determined after incubation for 18 hours at 37° C. and are shown in Table 3.

In the following Tables the following abbreviations are used:
NT—not tested
NG—no growth
C—contaminated

TABLE 1

MIC's (μg/ml) against Mycoplasma for Calcium Pseudomonate dehydrate

| ORGANISM | MIC (μg/ml) |
|---|---|
| M. hyopneumoniae NB12 | NG |
| M. hyopneumoniae JF 435 | 2.5 |
| M. hyopneumoniae HK (2) | 2.5 |
| M. hyopneumoniae Str 11 | 2.5 |
| M. hyopneumoniae J2206/183b | 2.5 |
| M. hyopneumoniae MS16 | 2.5 |
| M. hyopneumoniae PW/C/210 | 2.5 |
| M. hyopneumoniae LABER | 2.5 |
| M. hyopneumoniae UCD1 | 2.5 |
| M. hyopneumoniae TAM 6N | 2.5 |
| M. hyopneumoniae ATTCC 25095 | 2.5 |
| M. hyopneumoniae NCTC 10110 | 2.5 |
| + MEAN | 2.5 |
| M. hyorhinis ATCC 23234 | 1.0 |
| M. hyorhinis ATCC 25021 | 1.0 |
| M. hyosynoviae ATCC 25591 | 0.5 |
| M. bovis NCTC 10131 | .025 |
| M. bovigenitalium ATCC 14173 | 0.1 |
| M. dispar NCTC 10125 | NG |
| M. gallisepticum S6 | >10 |
| M. pneumoniae ATCC 15492 | 5 |

TABLE 2

MIC's (μg/ml) against Veterinary Bacteria for Calcium Pseudomonate dehydrate

| ORGANISM | MIC on Agar |
|---|---|
| E. coli NCTC 10418 | 80 |
| E. coli E1 | 80 |
| S. dublin S7 | 80 |
| S. typhimurium S18 | 80 |
| Bord. bronchiseptica BO8 | 5.0 |
| Bord. bronchiseptica BO9 | 1.3 |
| Past. multocida PA1 | .07 |
| Past. multocida PA2 | NG |
| Past. haemolytica PA5 | 2.5 |
| Erysipelothrix rhusiopathiae NCTC 8163 | 20 |
| Corynebacterium pyogenes CY1 | >80 |
| Staph. aureus B4 (pen.resistant) | .16 |
| Staph. aureus 152 (pen.sens.) | .16 |
| Staph. aureus Oxford | <.1 |
| Strep. suis (group D) SPS11 | .63 |
| Strep. uberis SPU1 | .07 |
| Strep. dysgalaciae SPD1 | .16 |
| Strep. agalactiae SPA1 | 0.16 |
| B. subtilis ATCC 6633 | .07 |
| Staph. aureus (Mexi) | .16 |
| Staph. aureus M60 | 0.16 |
| Moraxella Bovis | .31 |

TABLE 3

MIC's (μg/ml) against Human Bacteria for Calcium Pseudomonate dehydrate

| ORGANISM | MIC (μg/ml) |
|---|---|
| E. coli NCTC 10418 | 128 |
| E. coli ESS | 2 |
| R. mirabilis 889 | 128 |
| K. aerogenes A | >128 |
| P. aeruginosa 10662 | >128 |
| Pasteurella multocida 1633 | 0.5 |
| Haemophilus influenzaezae Q1 | 0.13 |
| Haemophilus influenzae Wy21 | 0.13 |
| Neisseria catarrhalis 1502 | 0.13 |
| Bacillus subtilis 6633 | 0.5 |
| Corynebacterium xerosis 9755 | >128 |
| Sarcina lutea 8340 | >128 |
| S. aureus Oxford | 0.13 |
| S. aureus Russell | 0.25 |
| S. aureus W2827 | 0.25 |
| S. aureus T2P− | 0.25 |
| S. aureus T22P− | 0.25 |
| S. aureus T63P+ | 0.25 |
| S. aureus T67P+ | 0.5 |
| S. aureus V331 | 0.5 |
| S. aureus V352 | 0.5 |
| S. pyogenes BcA | 0.5 |
| S. pyogenes CN10A | 0.03 |
| S. pyogenes 1947A | 0.13 |
| S. pyogenes 1953-A | 0.13 |
| S. agalactiae 2788-B | 0.5 |
| S. agalactiae 2798B | 0.5 |
| S. agalactiae 2866B | 0.5 |
| S. spp. 64/848-C | 0.5 |
| Streptococcus Spp 2465C | 0.5 |
| Streptococcus Spp 2761C | 0.5 |
| Streptococcus Spp 2373C | 0.5 |
| S. faecalis Tunisia | 128 |
| S. faecalis I(ER+) | 128 |
| S. faecalis PAGE | 128 |
| S. faecalis I | 128 |

TABLE 3-continued

MIC's (μg/ml) against Human Bacteria for Calcium Pseudomonate dehydrate

| ORGANISM | MIC (μg/ml) |
|---|---|
| S. pneumoniae CN33 | 0.03 |

We claim:
1. A hydrate of crystalline calcium pseudomonate.
2. Crystalline calcium pseudomonate dihydrate.
3. A hydrate of crystalline calcium pseudomonate substantially free of amorphous calcium pseudomonate.
4. Crystalline calcium pseudomonate dihydrate substantially free of amorphous calcium pseudomonate.
5. Anhydrous crystalline calcium pseudomonate substantially free of amorphous calcium pseudomonate.
6. A pharmaceutical or veterinary composition comprising a hydrate of crystalline calcium pseudomonate in combination with a pharmaceutically or veterinarily acceptable carrier or excipient.
7. The composition of claim 6 comprising a dihydrate of crystalline calcium pseudomonate.
8. A veterinarily acceptable premix formulation which comprises a hydrate of crystalline calcium pseudomonate in combination with a veterinarily acceptable carrier.
9. The premix formulation of claim 8 comprising a dihydrate of crystalline calcium pseudomonate.

* * * * *